US 6,638,223 B2

(12) United States Patent
Lifshitz et al.

(10) Patent No.: US 6,638,223 B2
(45) Date of Patent: Oct. 28, 2003

(54) OPERATOR INTERFACE FOR A MEDICAL DIAGNOSTIC IMAGING DEVICE

(75) Inventors: Ilan Lifshitz, Tel-Aviv (IL); Doron Hess, Haifa (IL)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 40 days.

(21) Appl. No.: 09/753,042

(22) Filed: Dec. 28, 2000

(65) Prior Publication Data

US 2002/0087061 A1 Jul. 4, 2002

(51) Int. Cl.⁷ .............................. A61B 5/05; A61B 8/00
(52) U.S. Cl. ..................... 600/440; 600/437; 700/17; 700/83
(58) Field of Search .................. 600/440, 437, 600/407; 700/17, 83; 345/173

(56) References Cited

U.S. PATENT DOCUMENTS

| | | | | |
|---|---|---|---|---|
| 4,509,526 A | * | 4/1985 | Barnes et al. | 600/456 |
| 5,293,326 A | * | 3/1994 | Arima et al. | 702/39 |
| 6,014,581 A | * | 1/2000 | Whayne et al. | 600/523 |
| 6,055,458 A | * | 4/2000 | Cochran et al. | 700/17 |
| 6,063,030 A | | 5/2000 | Vara et al. | 600/437 |
| 6,106,460 A | * | 8/2000 | Panescu et al. | 600/300 |
| 6,115,626 A | * | 9/2000 | Whayne et al. | 600/427 |
| 6,192,266 B1 | * | 2/2001 | Dupree et al. | 600/427 |

FOREIGN PATENT DOCUMENTS

EP   0 599 128   6/1994

OTHER PUBLICATIONS

European Search Report—International Application No. 01310622.4–2201 dated Aug. 16, 2002.

Hinckley et al., "The Props–Based Interface for Neurosurgical Visualization," Medicine Meets Virtual Reality. Global Healthcare Grid, San Diego, CA, USA pp. 552–562 (1997).

Lattanzi, J. et al., "Ultrasound–Based Stereotactic Guidance in Prostate Cancer—Quantification of Organ Motion and Set–Up Errors in External Beam Radiation Therapy." Computer Aided Surgery: Official Journal of the International Society for Computer Aided Surgery. United States, 5(4):289–295 (2000).

Ridley, "ITL brings Homegrown PACS to the masses" Radiology, Pacs Community, 'Online! pp. 1–2 (Nov. 1, 2000) Retrieved from the Internet: <URL:http://www.auntminnie.com>.

* cited by examiner

Primary Examiner—John Rivell
(74) Attorney, Agent, or Firm—McAndrews, Held & Malloy, Ltd.; Peter J. Vogel; Michael A. Dellapenna

(57) ABSTRACT

A method for providing operator control over a medical diagnostic device includes the steps of assigning each device function in a preselected device function set that implements a preselected medical diagnostic device to at least one function activation area on an image display. Subsequently, the method monitors a touchscreen for a touch, and determines a selected activation area based on the touch and the function activation area. Once the selected activation area is determined, the method performs a device function associated with the selected activation area.

23 Claims, 4 Drawing Sheets

OPERATOR INTERFACE FOR A MEDICAL DIAGNOSTIC IMAGING DEVICE

BACKGROUND OF THE INVENTION

The present invention relates to medical diagnostic imaging systems. In particular, the present invention relates to a user interface for a medical diagnostic imaging device.

Today, doctors and technicians have at their disposal a wide range of ultrasound, X-ray, nuclear, and other medical diagnostic imaging systems with which to examine patients. The capabilities of these medical diagnostic imaging systems have increased dramatically since their introduction. Spurred on by the development of inexpensive but very sophisticated, powerful, and fast processing circuitry, designers of medical diagnostic imaging systems continue to add and enhance a wide range of device functions for medical diagnostic imaging systems. Thus, for example, an ultrasound imaging system may include 2D or 3D imaging, Doppler overlay, Colorflow scans, image frame recording and playback capabilities, image annotation and archiving, zoom, panning, and the like.

The number and complexity of the device functions performed by medical diagnostic imaging system have increased to the point where many such peripheral devices include a full-sized keyboard and trackball as part of the user interface. The peripheral devices, however, increase the cost, complexity, and space required by the medical diagnostic imaging system. The keyboard, for example, is similar to that used on a home computer, and is required to direct the operation of the medical diagnostic imaging system. Doctors and technicians, however, are not computer scientists. In other words, the valuable time spent trying to understand and operate the peripheral devices of a medical diagnostic imaging system is better spent actually using the device to help a patient.

A need exists in the industry for a user interface for a medical diagnostic device that addresses the problems noted above and others previously experienced.

BRIEF SUMMARY OF THE INVENTION

A preferred embodiment of the present invention provides, in a medical diagnostic device, an operator interface for providing operator control over device functions of the medical diagnostic device. The operator interface includes a monitor for producing an image display, a touchscreen disposed in front of the monitor, and a plurality of activation areas defined on the image display. Each device function in a device function set that implements a preselected medical diagnostic device is associated with at least one of the activation areas so that no external input other than that supported by the touchscreen is required to operate the medical diagnostic device. In addition, a processor is coupled to the touch screen for detecting a touch on the touchscreen that identifies a selected activation area. The processor then performs the device function associated with the selected activation area.

A preferred embodiment of the present invention further provides a method for providing operator control over a medical diagnostic device. The method includes the steps of assigning each device function in a preselected device function set that implements a preselected medical diagnostic device to at least one function activation area on an image display. Subsequently, the method monitors a touchscreen for a touch, and determines a selected activation area based on the touch and the function activation area. Once the selected activation area is determined, the method performs a device function associated with the selected activation area.

DETAILED DESCRIPTION OF THE INVENTION

Figure 1:
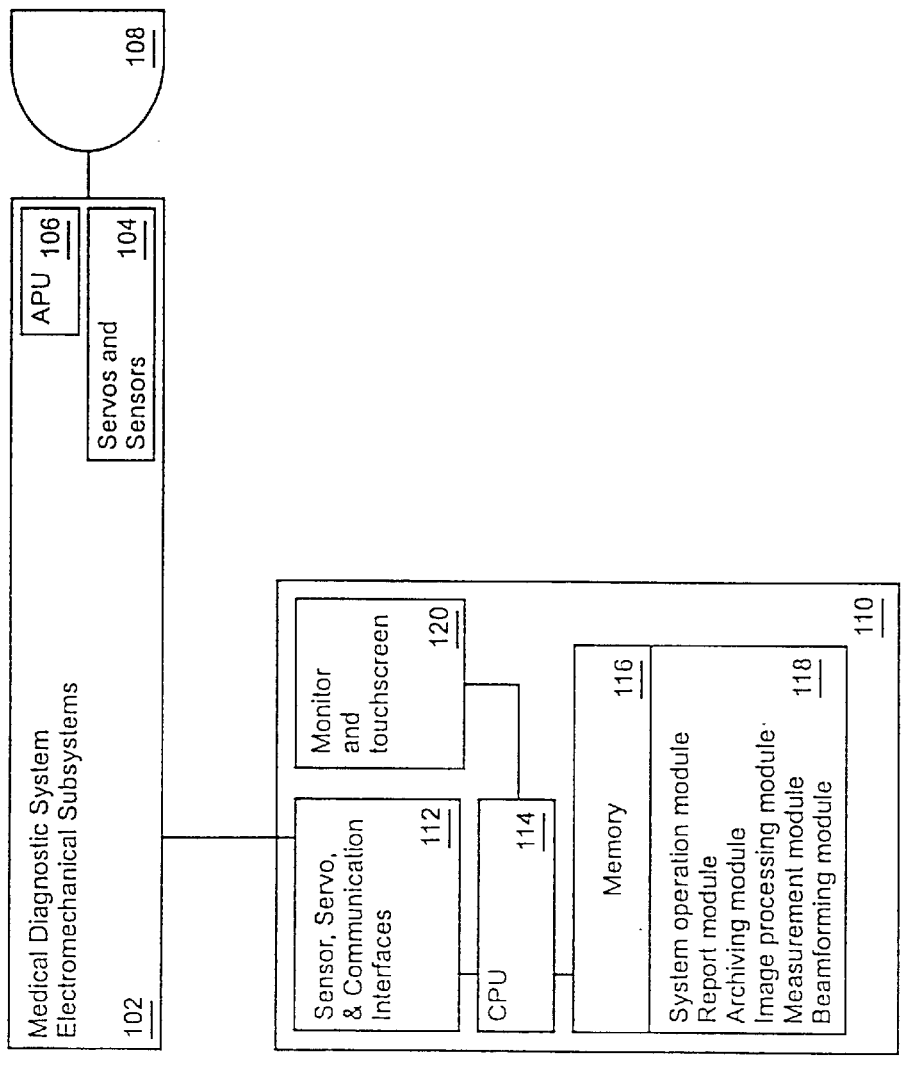
FIG. 1 shows a block diagram of a medical imaging device.

Turning first to FIG. 1, that figure shows one exemplary implementation of a medical imaging system 100. The medical imaging system 100 includes an electromechanical subsystem 102 which implements the electronic and mechanical subsystems of a medical imaging system apart from the computer software, monitor, and touchscreen interface discussed below. The electromechanical subsystem 102, depending on the particular imaging system implemented, may incorporate, for example, mechanical motor servos and feedback sensors 104, a magnet, X-ray image detectors, or an Acoustic Power Unit (APU) 106 coupled to an ultrasound scanner 108. In other words, the medical imaging system 100 may be implemented as any desired diagnostic system, including an MRI system, X-ray system, ultrasound system, electron microscope, heart monitor system, and the like.

Also shown in FIG. 1 is a system computer 110, that includes an electromechanical subsystem interface 112, a processor 114, and a memory 116. The memory 116 stores instructions for execution by the processor 114. Also illustrated in FIG. 1 is a touchscreen 120. The touchscreen 120 couples to the processor 114 and, in conjunction with the functional modules, provides complete control over the medical imaging system 100. In other words, no additional external input is required from, for example, a touchscreen, a trackball, function keys, and the like. The touchscreen 120 may be implemented as a resistive, capacitive, or other touchscreen that provides an indication to the processor 114 that an operator has touched the touchscreen 120 and a location of the touch.

The memory 116 stores instructions that implement the device functions of the functional modules of a preselected medical imaging system (e.g., an ultrasound imaging system). Such modules include a systems operation module, a report module, an archiving module, an image processing module, a measurement module, and a beamforming module, as examples. Additional functional modules are discussed below in conjunction with FIG. 2.

Figure 2:
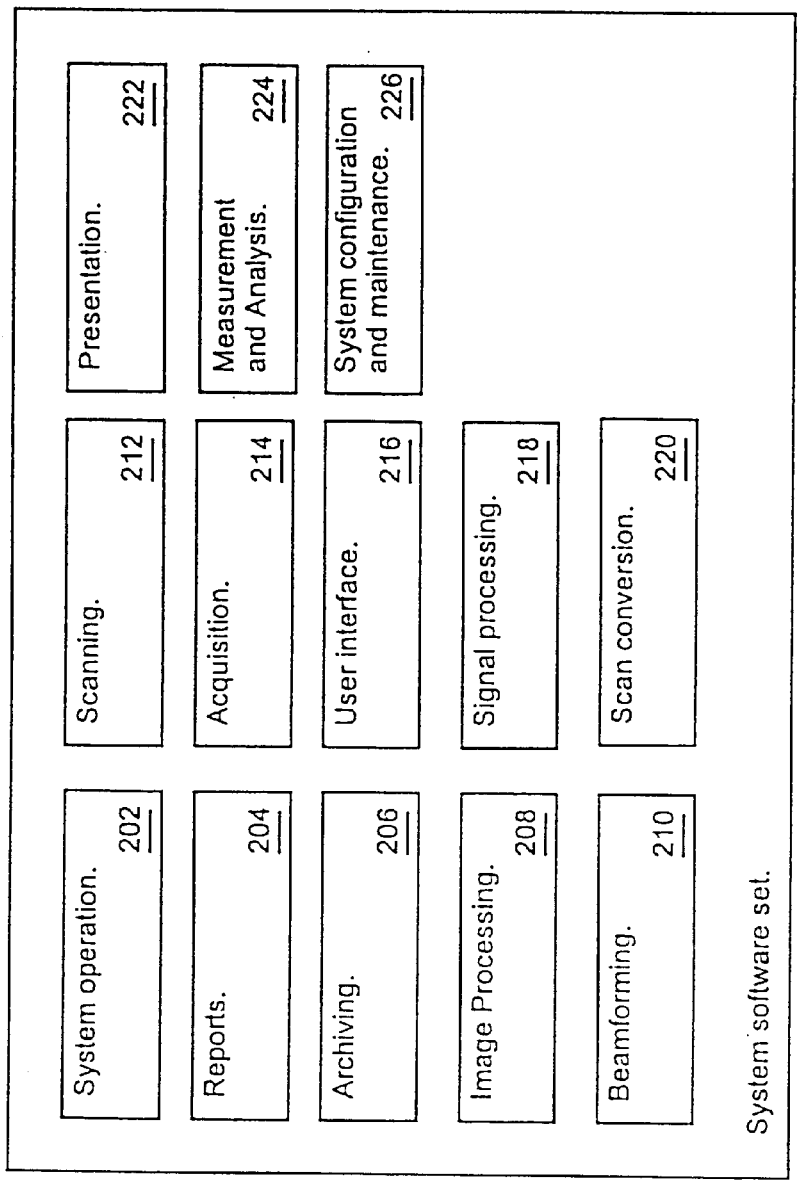
FIG. 2 shows functional modules that may be selected to form a complete device function set for a desired medical imaging device.

Turning to FIG. 2, that figure shows functional modules 200 that may be selected to form a complete device function set (i.e., a complete set of system software that implements a medical imaging device). The functional modules 200 implement one or more device functions and include a system operation module 202, report module 204, archiving module 206, image processing module 208, beamforming module 210, scanning module 212, acquisition module 214, user interface module 216, signal processing module 218, scan conversion module 220, presentation module 222, measurement and analysis module 224, and a diagnostic system configuration and maintenance module 226. The functional modules 200 include modules that may be used to implement, for example, an ultrasound diagnostic system. Certain functional modules may operate independently of other functional modules. Some functional modules, however, may pass intermediate results or partially processed data to other functional modules for further processing. The functional modules noted above are exemplary only. In other words, additional functional modules may be added for other any other tasks to be performed by a given medical diagnostic system, such as an external communication module.

The system operation module 202 carries out system control functions. As examples, the system operation module 202 may include device functions to directly control the electromechanical subsystem 102 to drive motor servos, evaluate sensor feedback, and initiate and terminate an ultrasound imaging sequence.

The report module 204 executes patient reporting device functions. The patient reporting device functions may include, for example, querying of patient images from the archiving module 206, and preparation, display, and printing of patient examination records, billing records, and patient contact information.

The archiving module 206 is responsible for device functions that maintain database records related to the operation of the diagnostic system. The database records may include patient examination images (either static images or image sequences (e.g., MPEG2 or other compressed or non-compressed movies)), operation and maintenance statistics (e.g., the time, date, and examination type for each use of the diagnostic system, and its service history), patient contact, billing, and examination records, including physician diagnoses, and the like.

The image-processing module 208 is responsible for device functions associated with manipulation of images (still or video) generated by the diagnostic system. Thus, as examples, the image-processing module may provide image contrast enhancement, image cropping, resolution enhancement, and other image processing functions. The image-processing module 208 typically allows the operator to retrieve, examine, modify, print, and save processed images, for example, by communicating with the database maintained by the archiving module 206. The image-processing module may also perform volume rendering to construct 3-dimensional models from a series of 2-dimensional B-mode or Doppler data sets of images using known volume rendering techniques.

The beamforming module 210 is responsible, for example, for device functions for controlling beamforming required to generate images in an ultrasound imaging system. Thus, the beamforming module 210 may receive raw data representing ultrasound echo information, apply the appropriate steering and gain corrections to the raw data, and output processed data sets ready for scan conversion for display as B-mode, Doppler, colorflow, or other image types.

The scanning module 212 handles user interface events received from the user interface module 216, determines the mode of an ultrasound scan to be taken, and passes the appropriate scan parameters to the acquisition module 214. The acquisition module 214 device functions handle requests for scan parameter changes, implements the scan parameter changes, and translates scan parameters if required by the hardware with the ultrasound scanner 108.

The acquisition module 214 executes scan sequences in the operator selected manner, and transfers hardware events (e.g., overpower, scanner disconnect, and the like), for example, to the system operation module 202 for error handling. The acquisition module 214 also receives ultrasound data sets that have been collected and formed by the beamforming module 210 and relays the data sets to the presentation module 222.

The user interface module 216 implements, preferably, functional menus, displays scan parameters, and monitors operator interface hardware, including keyboard control panels and trackballs (if included). The user interface module 216 handles device functions such as displaying and moving images and text and delegating touchscreen events, menu events, keyboard panel events, and trackball events to the scanning module 212 and other modules. As one example, an image processing function menu may be displayed that allows the user to increase brightness, decrease brightness, increase contrast, decrease contrast, and the like.

The signal-processing module 218 provides those device functions for processing of data sets acquired from the electromechanical subsystem 102 based upon the current mode of operation. The signal-processing module 218 may, for example, perform vector processing, including Doppler and Color Flow processing on the data sets.

The scan conversion module 220 device functions convert data between coordinate systems. Thus, for example, the scan conversion module 220 may convert data sets in the polar coordinate system to the Cartesian coordinate system for ready display on a typical video monitor.

The presentation module 222 device functions process and display ultrasound image information, including static images, video images, traces, and the like. The presentation module 222 is preferably adapted to display, additionally, Doppler and Color Flow images.

The measurement and analysis (M&A) module 224 provides device functions to implement an interface that allows the operator to examine the data returned during patient examination. As one example, the M&A module may allow the operator to determine blood flow velocity, perform volume measurements, perform 2-dimensional measurements such as determining cross sectional area and blood vessel diameter, perform cardiology or radiology analyses (e.g., locating of heart defects or tumors), increasing or decreasing scan depth of ultrasound focus, moving a Region of Interest box, positioning a Doppler gate, changing focus location, and the like.

The diagnostic system configuration and maintenance (C&M) module 226 is responsible for interfacing with the archiving module 206 to track maintenance history for the diagnostic system. Thus, for example, the C&M module 226 preferably allows a technician to enter the results of routine or non-routine maintenance calls, allow operators to submit maintenance requests, and the like. The C&M module also allows an operator to perform initial setup and configuration operations on the diagnostic system.

A voice reognition module (not shown) may also be provided to allow the medical imaging system 100 to respond to operator voice input.

The functional modules 200 may be selected to implement any desired medical diagnostic system. In a preferred implementation, the functional modules 200 are chosen to implement a complete device function set for an ultrasound system, and therefore include functional modules specifically directed to ultrasound imaging, for example, the beamforming module 210, scanning module 212, and scan conversion module 220. The device function set differs between diagnostic systems, however. As one example, an X-ray imaging system may include a linear tomographic scan control module, rather than a beamforming module, and a servo motor system used to move an X-ray source. Thus, although the present discussion proceeds primarily with reference to an ultrasound diagnostic system, it is noted that any device function set may be used by determining which functional modules to include in the device function set for a given diagnostic system.

Figure 3:
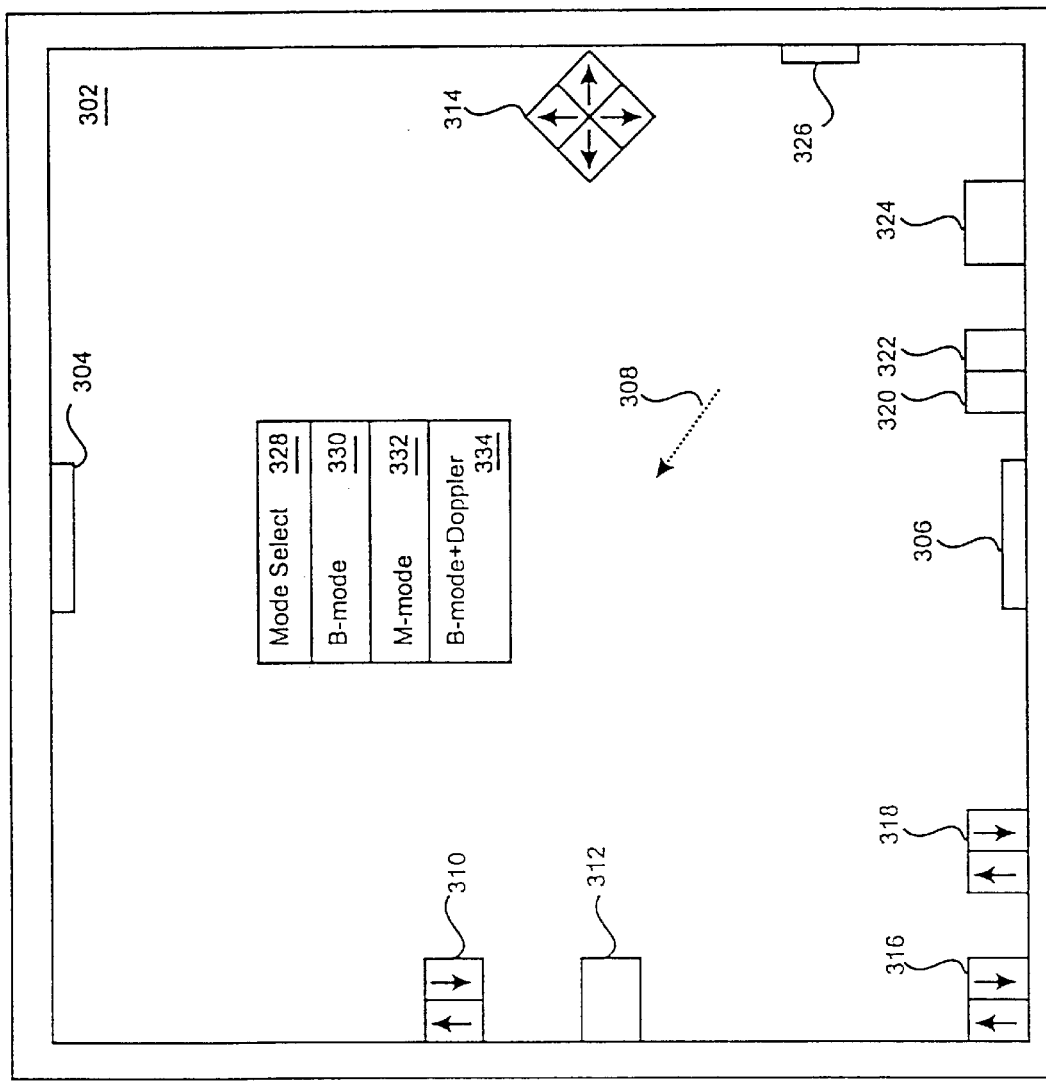
FIG. 3 shows an ultrasound imaging system monitor with touchscreen and function activation area layout.

Turning now to FIG. 3, that figure shows an ultrasound system monitor 300 with touchscreen 302. The touchscreen 302 is positioned in front of the monitor 300 that presents an image display of graphics and text associated with operation of the imaging system 100, including B-mode images, Doppler images, text labels, and the like. Numerous activation areas and pop up menus are defined on the image display, including a penetration depth increase activation area 304 and a penetration depth decrease activation area 306. A drag indicator 308 illustrates the operation of touching the touchscreen 302 and dragging a finger, pen, or other pointer in the direction of the drag indicator 308.

Additional activation areas include the zoom activation area 310, the store image activation area 312, and the movement activation area 314. A brightness control activation area 316, a contrast control activation area 318, an image rotate activation area 320, and an image print activation area 322 are also defined. Additionally, FIG. 3 shows a blood flow measurement activation area 324, and a mode select activation area 326.

The activation areas may be defined in location and size as absolute pixel regions on the display. For example, the zoom activation area 310 may defined as a rectangle of 100 pixels by 50 pixels centered at pixel 0,400. As shown in FIG. 3, the zoom activation area 310 (as well as the brightness and contrast activation areas 316 and 318) may be divided into two sections, one for increased zoom (e.g., shown as an up-arrow) and one for decreased zoom (e.g., shown as a down-arrow). In other embodiments, the activation areas may be defined relative to one another in position and size. The activation areas need not be rectangular. Rather, the activation areas may be circular, elliptical, and the like.

The penetration depth increase activation area 304 and the penetration depth decrease activation area 306 allow the operator to perform the device functions of increasing or decreasing the penetration depth of ultrasound energy into the body. Thus, when the operator touches inside the penetration depth increase activation area 304, the processor 114 identifies the penetration depth increase activation area 304 as a selected function activation area, and increases the penetration depth of transmitted ultrasound energy. Similarly, when the operator touches inside the zoom activation area 310, the processor 114 increases or decreases the zoom level appropriately.

Each device function in a device function set that implements the medical imaging system 100 is associated with at least one of the function activation areas or pop up menus. As a result, the activation areas and pop up menus cover all of the device functions implemented by the medical imaging system 100. In other words, the touchscreen 302 alone may be used to control the medical imaging system 100 in its entirety and no additional input from other sources (e.g., a keyboard or trackball) is required to operate the medical imaging system 100. To this end, and as examples, the store image activation area 312 allows the operator to perform the device functions of storing the current image in an archive, the brightness and contrast activation areas 316 and 318 allow operator manipulation of brightness and contrast, and the movement activation area 314 allows the operator to perform the device functions of moving a cursor, ROI box, image, or text label in any direction as indicated by the specific directional activation areas associated with the movement activation area 314.

As additional examples, the processor 114 identifies as selected function activation areas (when touched) the image rotate activation area 320 (e.g., to rotate an image ninety degrees), the image print activation area 322 (e.g., to print the image to an attached or network printer), and the measurement activation area 324 (e.g., to begin displaying measurements of blood flow velocity, volume, and the like). Furthermore, it is noted that the mode select activation area 326 may be used to select a particular imaging mode for the medical imaging system 100. Thus, the mode select activation area 326 may be used to select in a cyclic manner through repeating touches B-mode, M-mode, B-mode plus Doppler, B-mode plus colorflow imaging modes, and the like.

Additionally, the processor 114 may present pop up function menus to the operator on the monitor 300. Thus, for example, as an alternative to cycling through imaging modes by touching the mode select activation area 326, the processor may present the pop up mode selection menu 328. The mode selection menu 328 as illustrated includes the following function menu activation areas: a B-mode activation area 330, an M-mode activation area 332, and a B-mode plus Doppler activation area 334. When the mode selection menu 328 is presented, the operator touches an appropriate activation area 330–334 to choose an imaging mode. Of course, additional pop up function menus with individual activation areas for mode specific functions, for example, may also be implemented for any number of device functions (e.g., measurement and analysis and calibration device functions) and displayed when the operator touches a predetermined pop up menu location on the monitor 300, or in response to a previous touchscreen menu selection.

Note also that the processor 114 allows the user to drag images and text as indicated by the drag indicator 308. Thus, for example, the operator may place a text label on the display by dragging it using the touchscreen 302. When general purpose input is required (e.g., in order to select a filename for saving an image, or to select a patient), the medical imaging system 100 may display a keyboard image on the monitor 300 with each keyboard key defined by a rectangular box or pixel area. Thus, the user may type on the screen using a soft-keyboard, rather than resort to a separate physical keyboard. Optionally, the medial imaging system 100 includes character recognition software that allows the operator to use a finger, pen, or other pointer on the touchscreen to enter characters. Thus, for example, a vertical drag on the touchscreen may be interpreted as the letter 'l', while a cross on the touchscreen may be interpreted as the letter 't', and the like.

Note that the activation areas described above are exemplary only, and that many other arrangements and designs of activation areas, pop up controls, pop up menus, and the like are also suitable.

The touchscreen 302 provides an enhanced degree of interactivity with the images and text displayed on the monitor 300. Thus, a drag operation (e.g., as shown by the drag indicator 308) may be used to position on-screen objects, set range gates, set focus depth and location, zoom in and out, rotate images, move a ROI box, and the like. As another example, the processor 114 may interpret touches on the touchscreen 302 to select one or more simultaneously displayed windows as "active" (i.e., to direct the processor to continue to update or to freeze updates of a Doppler or 2D display window), to set scan depths, to change focus location, and the like. Thus, the operator may alternate between, for example, simultaneous 2D, Colorflow, Doppler, and zoom modes using the touchscreen to make any of the modes active, and to set the appropriate ROI active for size and location changes.

The processor 114 tracks the current operational mode of the medical imaging system 100. Thus, in response to a touch on the touchscreen 302, the processor may pop up one or more menus appropriate for the current operational mode (e.g., a Doppler function menu or B-mode function menu that include the functions of interest in the current operational mode). As another example, the processor 114 may display mode specific pop up controls for such features as a video cassette or DVD recorder (e.g., play, pause, record, fast forward, and the like) or time gain compensation modes (e.g., gain selection).

Figure 4:
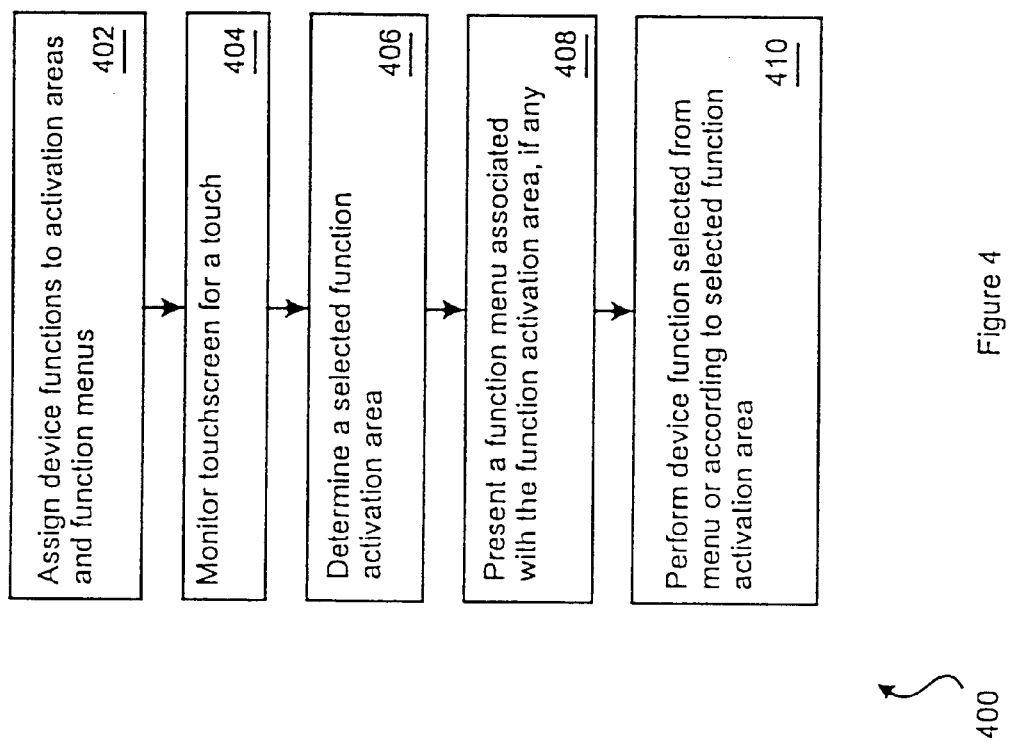
FIG. 4 shows a high level flow diagram of the user interface processing that occurs in the ultrasound imaging system.

Turning next to FIG. 4, that figure illustrates a flow diagram 400 of the operation of the touchscreen user interface. At step 402, the processor 114 assigns each device function in a device function set that implements the medical imaging system 100 to activation areas and function menus. At step 404, the processor monitors the touchscreen for a touch. When a touch is detected, the processor 114 determines to which, if any, activation area the touch corresponds (step 406). The touched activation area is referred to as the selected function activation area. Subsequently, at step 408, the processor 114 presents a function menu, if any, associated with the selected function activation area. At step 410, the processor 114 performs the device function assigned to the selected function activate area or selected from the function menu.

While the invention has been described with reference to its preferred embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. In a medical diagnostic device, an operator interface for providing operator control over device functions of the medical diagnostic device, the operator interface comprising:

a monitor producing an image display;

a touchscreen disposed in front of the monitor;

a memory storing device function sets, the device function sets each comprising a plurality of device functions, at least one of the device functions comprising direct control over an electromechanical subsystem of the medical diagnostic device, the device function sets providing complete control over a preselected medical diagnostic device;

a plurality of activation areas defined on the touchscreen, the plurality of activation areas providing access to all the device function sets, each activation area being associated with at least one device function;

a processor coupled to the touch screen for detecting a touch on the touchscreen that identifies a selected activation area, the processor performing the device function associated with the selected activation area;

a data recording device coupled to the processor, the data recording device being external to the medical diagnostic device, the device function sets including the device functions that implement the data recording device, the plurality of activation areas including at least one of play, pause, record, fast forward and stop for controlling the data recording device.

2. The operator interface of claim 1, wherein the processor presents a pop up function menu with a plurality of function menu activation areas in response to the touch.

3. The operator interface of claim 1, wherein the device function sets include image processing device functions.

4. The operator interface of claim 3, wherein the image processing device functions include zoom, scroll, and text label device functions.

5. The operator interface of claim 3, wherein the image processing device functions further include brightness and contrast adjustment device functions.

6. The operator interface of claim 1, wherein the device function sets include measurement and analysis device functions and maintenance device functions.

7. The operator interface of claim 1, wherein the processor is responsive to a drag on the touchscreen to position at least one of text and graphics.

8. The operator interface of claim 1, wherein at least one of the activation areas defines a movement activation area having a plurality of associated directional activation areas.

9. The operator interface of claim 1, the memory further comprising storing character recognition software, the processor detecting the touch on the touchscreen and interpreting the touch as a character.

10. The operator interface of claim 1, the monitor producing the image display in at least two simultaneously displayed windows, the processor detecting the touch on the touchscreen and identifying the selected activation area as being associated with one displayed window, the processor making the displayed window active.

11. The operator interface of claim 1, the device function sets further including a keyboard function for general purpose input, the monitor displaying each keyboard key defined by one of a rectangular box and pixel area.

12. A method for providing operator control over a medical diagnostic device, the method comprising:

defining function activation areas on an image display comprising a touchscreen through which device functions may be selected, at least one of the device functions comprising direct control over an electromechanical subsystem of the medical diagnostic device, the device functions being included in device function sets including a keyboard function for general purpose input, the image display displaying each keyboard key defined by one of a rectangular box and pixel area, the function activation areas providing access to all the device functions providing control over a preselected medical diagnostic device;

monitoring the touchscreen for a touch;

determining a selected activation area based on the touch and the function activation areas; and performing a device function associated with the selected activation area.

13. The method of claim 12, further comprising presenting a pop up function menu in response to the selected activation area and monitoring the touchscreen for a selected function menu activation area.

14. The method of claim 13, wherein performing comprises performing a device function associated with the selected function menu activation area.

15. The method of claim 13, wherein presenting comprises presenting a function menu having a plurality of function menu activation areas.

16. The method of claim 12, wherein the device function is selected from device functions supported by an image processing module.

17. The method of claim 12, wherein the preselected medical diagnostic device is an ultrasound imaging system.

18. The method of claim 12, the defining step further comprising defining the function activation areas as absolute pixel regions on the image display.

19. The method of claim 12, the defining step further comprising defining the function activation areas relative to one another in at least one of location and size.

20. An ultrasound imaging system providing touchscreen based operator control, the ultrasound imaging system comprising:

an ultrasound scanner coupled to an acoustic power unit;

a processor coupled to a memory and the ultrasound scanner;

a monitor coupled to the processor for providing an image display;

a touchscreen disposed in front of the monitor and coupled to the processor;

a plurality of activation areas defined on the touchscreen, wherein each device function is obtainable through at least one of the activation areas, device function sets including all the device functions that implement a preselected medical diagnostic device, at least one of the device functions comprising direct control over an electromechanical subsystem of the ultrasound imaging system, the device function sets further including a keyboard function for general purpose input, the monitor displaying each keyboard key defined by one of a rectangular box and pixel area; and wherein the processor is responsive to detect a touch on the touchscreen that identifies a selected activation area, the processor performing the device function associated with the selected activation area.

21. The ultrasound imaging system of claim 20, wherein the device function sets include beamforming functions and image processing device functions.

22. The ultrasound imaging system of claim 20, wherein the device function sets further include image archiving device functions and display presentation functions.

23. The ultrasound imaging system of claim 20, further comprising a data recording device coupled to the processor, the data recording device being external to the ultrasound imaging system, the device function sets including the device functions that implement the data recording device, the plurality of activation areas including at least one of play, pause, record, fast forward and stop for controlling the data recording device.

* * * * *